US012502245B2

(12) United States Patent
Anthony et al.

(10) Patent No.: US 12,502,245 B2
(45) Date of Patent: Dec. 23, 2025

(54) BRAIDED FIDUCIAL METALLIC MARKER SYSTEM

(71) Applicant: Surgical Radiation Products, LLC, North Palm Beach, FL (US)

(72) Inventors: Lori A. Anthony, North Palm Beach, FL (US); John D. Corbitt, Jr., Palm Beach Gardens, FL (US)

(73) Assignee: Surgical Radiation Products, LLC, Lake Worth, FL (US)

( * ) Notice: Subject to any disclaimer, the term of this patent is extended or adjusted under 35 U.S.C. 154(b) by 1059 days.

(21) Appl. No.: 16/360,991

(22) Filed: Mar. 21, 2019

(65) Prior Publication Data

US 2020/0297453 A1 Sep. 24, 2020

(51) Int. Cl.
*A61B 90/00* (2016.01)
*A61B 17/06* (2006.01)

(52) U.S. Cl.
CPC ........ *A61B 90/39* (2016.02); *A61B 17/06166* (2013.01); *A61B 2017/06171* (2013.01); *A61B 2090/3908* (2016.02); *A61B 2090/392* (2016.02); *A61B 2090/3962* (2016.02); *A61B 2090/3991* (2016.02)

(58) Field of Classification Search
CPC ............ A61B 90/39; A61B 2090/3904; A61B 2090/3966; A61B 17/06166
See application file for complete search history.

(56) References Cited

U.S. PATENT DOCUMENTS

| | | | | |
|---|---|---|---|---|
| 2,153,889 | A | 4/1939 | Hames | |
| 9,669,113 | B1 * | 6/2017 | Sirimanne | A61K 49/006 |
| 2006/0004440 | A1 * | 1/2006 | Stinson | A61L 27/50 623/1.34 |
| 2006/0173296 | A1 * | 8/2006 | Miller | A61B 90/39 600/431 |
| 2007/0093726 | A1 * | 4/2007 | Leopold | A61B 90/39 600/562 |
| 2007/0233175 | A1 * | 10/2007 | Zaver | A61F 2/0105 606/200 |

(Continued)

FOREIGN PATENT DOCUMENTS

| | | |
|---|---|---|
| DE | 2949920 | 3/1981 |
| WO | WO2009151876 | 12/2009 |

*Primary Examiner* — Anh Tuan T Nguyen
*Assistant Examiner* — Younhee Choi
(74) *Attorney, Agent, or Firm* — McHale & Slavin, P.A.

(57) ABSTRACT

A braided suture fiducial metallic marker system includes a braided suture fiducial metallic marker system includes a metallic marker, a multiplicity of suture threads (absorbable or non-absorbable), braided with one another and encapsulating the marker, and a needle disposed at a distal end of the multiplicity of threads and a needle disposed at an opposite distal end. In this regard, a portion of the braided suture threads in which the marker is encapsulated may be visually demarcated with a contrasting color. As well, the marker may define a cavity which may in turn, contain a radioactive material. As another option, a single one of the multiplicity of suture threads may extend through one end of the cavity to another end of the cavity so that the single one of the multiplicity of threads is braided with others of the multiplicity of suture threads.

10 Claims, 1 Drawing Sheet

(56) References Cited

U.S. PATENT DOCUMENTS

| | | | | |
|---|---|---|---|---|
| 2008/0051870 | A1* | 2/2008 | Kaufmann | A61B 90/39 623/1.11 |
| 2008/0269603 | A1* | 10/2008 | Nicoson | A61B 90/39 600/431 |
| 2009/0216063 | A1 | 8/2009 | Lamoureux et al. | |
| 2009/0234384 | A1 | 9/2009 | Hadba | |
| 2010/0121130 | A1 | 5/2010 | Lamoureux | |
| 2011/0202085 | A1* | 8/2011 | Loganathan | A61B 17/12022 606/200 |
| 2011/0264138 | A1* | 10/2011 | Avelar | A61B 90/94 606/228 |
| 2014/0074158 | A1* | 3/2014 | Feezor | A61B 17/0482 606/228 |
| 2014/0257378 | A1 | 9/2014 | Norton et al. | |
| 2018/0049875 | A1* | 2/2018 | Iflah | A61B 17/0401 |
| 2018/0344429 | A1* | 12/2018 | Stewart | A61B 90/90 |

* cited by examiner

BRAIDED FIDUCIAL METALLIC MARKER SYSTEM

CROSS-REFERENCE TO RELATED APPLICATIONS

This application is related to U.S. patent application Ser. No. 15/078,068, filed Mar. 23, 2016, which is a Divisional Application of U.S. patent application Ser. No. 13/348,965, filed Jan. 12, 2012, now U.S. Pat. No. 9,320,517, the entirety of each which is incorporated herein by reference.

BACKGROUND OF THE INVENTION

Field of the Invention

The present invention relates to the field of medical imaging and more particularly to a fiducial metal marker secured to a suture.

Description of the Related Art

A fiducial metal marker is a metallic object placed in the field of view of an imaging system which appears in the image produced, for use as a point of reference or a measure. In the context of medical imaging, a fiducial metal marker is a metallic reference point used to assist the health care provider in maintaining a target area within the field of view to ensure accurate results for the patient. More specifically, in the context of radiation therapy for cancer, a fiducial metal marker marks the tumor or tumor bed and facilitates precise delivery of radiation energy in treating the marked tumor or tumor bed while sparing surrounding healthy tissue from the effects of the radiation energy.

During use, one or more metal markers typically spheres or cylinders that may be gold, Platinum, Iridium, or other preferred metals, are inserted into the target tissue. Through the use of a suture on a needle or a needle injection system, these markers can be placed in a desired location. In many instances the insertion of the marker is done with the assistance of an image guided operation. If these markers are placed with a needle injection system, the needle system is removed leaving only the marker in place. If the suture marker system is used then the marker will be left behind as well as a portion of the suture holding it in place. Dense tissue will hold the marker in place so as to insure accurate targeting of a radiation beam, however less dense tissue and fatty tissue will not hold a loose marker accurately. If a suture marker system is used on the less dense tissue then it can be sutured into the tissue and tied so as not to move away from the desired location. A suture marker system that is tied into place is obviously a more reliable system.

To address the unique challenges presented by breast or fatty tissue in fiducial metallic marker placement, suture type marker system have been used quite effectively in targeted beam radiation therapy. In this regard, the intermediate suture is secured to the marker through a hollow channel defined within the marker. In this way the marker has been positioned at the desired location into the tissue. By sewing the marker in place we can prevent movement or migration of the metallic marker away from our desired location. Thus, limiting the amount of radiation exposure to adjacent healthy tissue and organs.

BRIEF SUMMARY OF THE INVENTION

The present invention describes an improvement to the suture marker system by way of attaching the marker to the suture in a new braided woven technique. In one embodiment of the system the metallic marker is contained within the braided suture, absorbable or non-absorbable fibers, in this way securing the marker inside of the suture. In this regard, the marker becomes secured inside to the woven suture threads and may be palpable along the suture thread or can alternatively be demarcated with a contrasting color. As well, the metallic marker (which is a cylinder) may contain radioactive material inside of it. As another option a single one of the multiplicity of the suture threads may extend through one end of the cavity to another end of the cavity so that the single one of the multiplicity of threads is braided with others of the multiplicity of suture threads.

In another embodiment of the invention, a method for assembling a braided suture fiducial metallic marker system includes inserting a metallic marker amongst a multiplicity of suture threads at a longitudinal focal point of the suture threads. The method further includes braiding the multiplicity of suture threads around the metallic marker so as to encapsulate the metallic marker. Finally, the method includes securing a needle to a distal end of the suture thread. Optionally, the method includes visually demarcating a portion of the braided multiplicity of suture threads wherein the metallic marker is encapsulated.

Additional aspects of the invention will be set forth in part in the description which follows, and in part will be obvious from the description, or may be learned by practice of the invention. The aspects of the invention will be realized and attained by means of the elements and combinations particularly pointed out in the appended claims. It is to be understood that both the foregoing general description and the following detailed description are exemplary and explanatory only and are not restrictive of the invention, as claimed.

BRIEF DESCRIPTION OF THE SEVERAL VIEWS OF THE DRAWINGS

The accompanying drawings, which are incorporated in and constitute part of this specification, illustrate embodiments of the invention and together with the description, serve to explain the principles of the invention. The embodiments illustrated herein are presently preferred, it being understood, however, that the invention is not limited to the precise arrangements and instrumentalities shown, wherein.

DETAILED DESCRIPTION OF THE INVENTION

Embodiments of the invention provide for a braided suture fiducial metallic marker system. The system includes a marker affixed to a strand of suture thread such as an absorbable suture or a non-absorbable suture. The strand of suture thread is secured to additional strands of suture thread in a braid. Of importance, the braid wovenly encapsulates the marker. At least one end of the braid is then secured to a needle. Optionally, the marker includes a cavity that may include a radioactive material. As well, the outer portion of the braid may be denoted with a color that is different than the color of the suture thread so as to indicate the position of the marker encapsulated therein.

Figure 1:
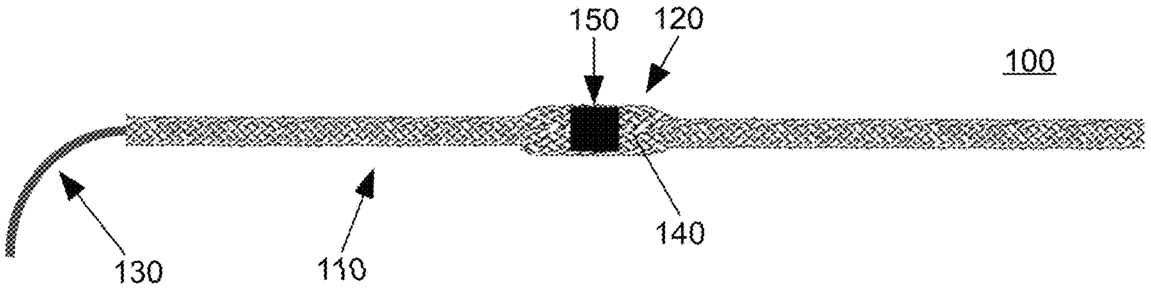
FIG. 1 is perspective view of a braided suture fiducial metallic marker system.

In further illustration, FIG. 1 is perspective view of a braided suture fiducial metallic marker system. As shown in FIG. 1, a braided suture fiducial metallic marker system 100 includes a marker 140 encapsulated within an encapsulating portion 120 of a braided suture 110 formed from individual suture threads braided together. Each of the suture threads may be a "0" size suture, or alternatively a "1" size suture, a "2/0" suture, or a smaller "3/0" or "4/0" suture, or even a smaller "6/0" suture. The braided suture 110 in turn is coupled to a needle 130 at an end of the braided suture. Optionally, the encapsulating portion 120 of the braided suture 110 is visually demarcated with a contrasting color 150 so as to indicate a location in the braided suture 110 of the marker 140.

Figure 2:
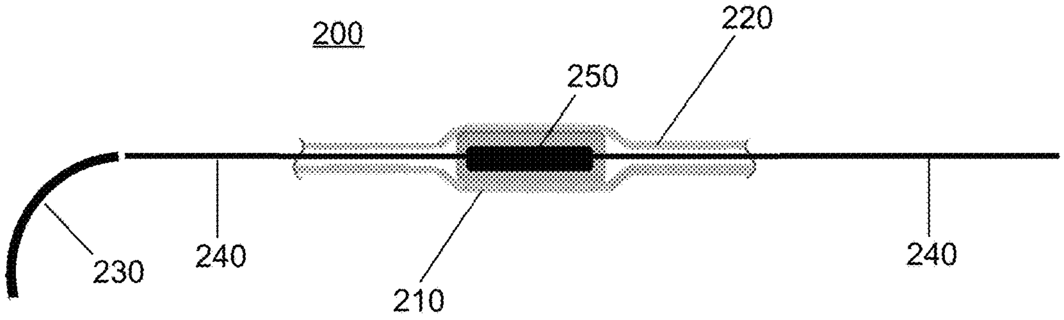
FIG. 2 is cut-away side view of an encapsulating portion of the braided suture fiducial metallic marker system of FIG. 1; and, FIG. 3 is a pictorial illustration of a process for assembling the braided suture fiducial marker system of FIG. 1.

Turning now to FIG. 2, a cut-away side view of an encapsulating portion of the braided suture fiducial metallic marker system of FIG. 1 is provided. As can be seen in FIG. 2, the braided suture fiducial metallic marker system 220 has a braided suture 220 that encapsulates a metallic marker 210 formed from a metal such as pure gold. The marker 210 is affixed to a single suture thread 240 that is braided with other suture threads to form the braided suture 220. A distal end of the single suture thread 240 is secured to a needle 230 as can be seen. Finally, the metallic marker 210 may be hollow, defining a cavity 250. The cavity 250 then may include a radioactive material so as to facilitate visualization in an imaging system. To that end, the metallic marker 210 may have the dimensions of 0.040"+/−0.001" outside diameter by 0.030"+/−0.001" inside diameter by 0.175"+/−0.005" length. The marker is metallic. In one aspect of the embodiment, the marker may be formed of pure gold. Alternatively, the marker may be formed of platinum or iridium, or a combination of gold and platinum, or gold and iridium, or platinum and iridium.

Figure 3:
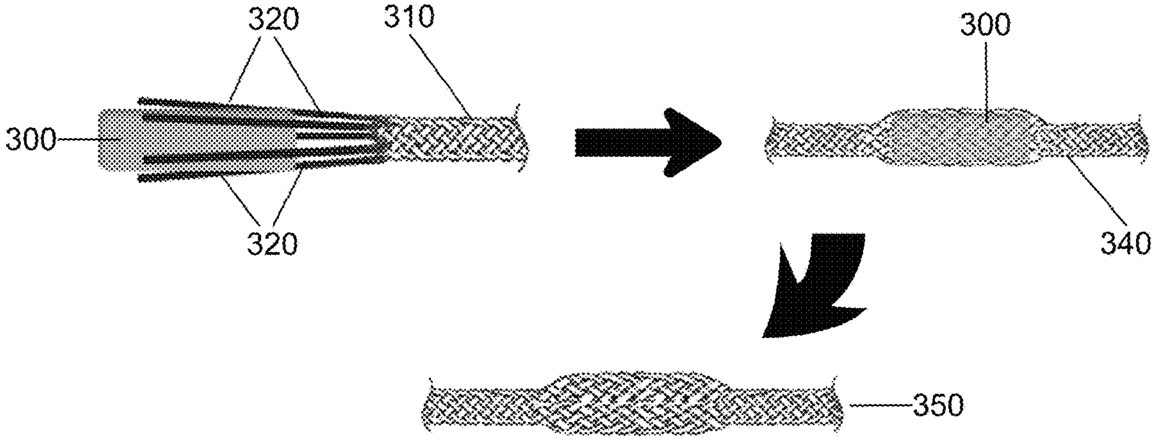

The braided suture fiducial metallic marker system 200 of FIG. 2 may be assembled through a braiding process. In further illustration, FIG. 3 pictorially shows a process for assembling the braided suture fiducial marker system of FIG. 1. As shown in FIG. 3, a marker 300 is inserted into a longitudinal focal point of a multiplicity of suture threads 320 surrounding the marker 300. The multiplicity of suture threads 320 are then braided with one another so as to form an encapsulating portion 340 encapsulating the marker 300. The final product is a braided suture fiducial metallic marker system 350.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated.

Having thus described the invention of the present application in detail and by reference to embodiments thereof, it will be apparent that modifications and variations are possible without departing from the scope of the invention defined in the appended claims as follows:

We claim:

1. A braided suture fiducial metallic marker system comprising:

a metallic marker having a first end separated from a second end by a length;

a multiplicity of suture threads encapsulating said metallic marker within a marker encapsulating portion, said encapsulating portion defined by said multiplicity of suture threads braided contiguously to engage said first end, said second end, and said length therebetween of said metallic marker, and reducing in diameter at each end of said metallic marker to maintain said metallic marker in a fixed position within said marker encapsulating portion; and a needle disposed at a distal end of the multiplicity of suture threads.

2. The system of claim 1, wherein the marker encapsulating portion is visually demarcated with a contrasting color.

3. The system of claim 1, wherein the metallic marker defines a cavity.

4. The system of claim 3, wherein the cavity contains a radioactive material.

5. The system of claim 3, wherein a single one of the multiplicity of suture threads extends through one end of the cavity to another end of the cavity and is braided with others of the multiplicity of suture threads.

6. The system of claim 1, wherein the multiplicity of suture threads are absorbable suture threads.

7. The system of claim 1, wherein the multiplicity of suture threads are non-absorbable.

8. The system of claim 1, wherein the metallic marker is formed from pure gold.

9. The system of claim 1, wherein the metallic marker is formed from platinum.

10. The system of claim 1, wherein the metallic marker is formed from iridium.

* * * * *